(12) United States Patent
Kimura et al.

(10) Patent No.: US 8,777,919 B2
(45) Date of Patent: Jul. 15, 2014

(54) FASTENING TAB AND METHOD OF MAKING THE SAME

(75) Inventors: Shinji Kimura, Kanagawa (JP); Masato Kondo, Kanagawa (JP); Steven J. Perron, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 509 days.

(21) Appl. No.: 12/962,090

(22) Filed: Dec. 7, 2010

(65) Prior Publication Data

US 2012/0143166 A1 Jun. 7, 2012

(51) Int. Cl.
*A61F 13/15* (2006.01)
*A61F 13/56* (2006.01)

(52) U.S. Cl.
CPC ....... *A61F 13/5633* (2013.01); *A61F 13/15756* (2013.01)
USPC ............................................. 604/391; 24/306

(58) Field of Classification Search
USPC ..................... 604/389–391; 24/306, 912–919
See application file for complete search history.

(56) References Cited

U.S. PATENT DOCUMENTS

| | | |
|---|---|---|
| 4,699,622 A | 10/1987 | Toussant |
| 4,894,060 A | 1/1990 | Nestegard |
| 5,077,870 A | 1/1992 | Melbye |
| 5,312,387 A | 5/1994 | Rossini |
| 5,344,691 A | 9/1994 | Hanschen |
| 5,399,219 A | 3/1995 | Roessler |
| 5,487,809 A | 1/1996 | Goulait |
| 5,537,722 A | 7/1996 | Niederhofer |
| 5,554,146 A | 9/1996 | Niederhofer |
| 5,705,013 A | 1/1998 | Nease |
| 5,759,317 A | 6/1998 | Justmann |
| 5,851,205 A | 12/1998 | Hisada |
| 5,900,101 A | 5/1999 | Justmann |
| 5,957,908 A | 9/1999 | Kline |
| 5,985,081 A | 11/1999 | Reynolds |
| 6,030,373 A | 2/2000 | VanGompel |
| 6,051,094 A | 4/2000 | Melbye |

(Continued)

FOREIGN PATENT DOCUMENTS

| | | |
|---|---|---|
| EP | 0233704 | 8/1987 |
| EP | 0341993 | 11/1989 |

(Continued)

OTHER PUBLICATIONS

ASTM Designation: D 882-02. Standard Test Method for Tensile Properties of Thin Plastic Sheeting. Published Jun. 2002.

(Continued)

*Primary Examiner* — Melanie Hand
*Assistant Examiner* — Aundria Hairell

(57) ABSTRACT

A fastening tab is provided having a substrate with a main portion, a user's end portion extending from the main portion, a primary mechanical fastening patch having a side edge coterminous with the side edge of the user's end portion of the substrate, and first and second auxiliary mechanical fastening patches on the main portion of the substrate. A method of making a fastening tab is also disclosed. The method includes attaching multiple discrete patches of mechanical fastener to a substrate web extending in the machine direction, cutting through the substrate web and the multiple patches of mechanical fastener in the machine direction with a continuous, meandering cut to provide two sub-webs, and optionally providing cross-web direction cuts through each sub-web to provide a plurality of fastening tabs. An absorbent article including the fastening tab and webs of fastening tabs are also included.

20 Claims, 6 Drawing Sheets

(56) References Cited

U.S. PATENT DOCUMENTS

| | | |
|---|---|---|
| 6,075,179 A | 6/2000 | McCormack |
| 6,190,758 B1 | 2/2001 | Stopper |
| 6,406,468 B1 | 6/2002 | Dilnik |
| 6,419,667 B1 | 7/2002 | Avalon |
| 6,544,245 B2 | 4/2003 | Neeb |
| 6,575,953 B2 | 6/2003 | Olson |
| 7,032,278 B2 | 4/2006 | Kurtz, Jr. |
| 7,125,400 B2 | 10/2006 | Igaue |
| 7,361,246 B2 | 4/2008 | Chang |
| 7,371,302 B2 | 5/2008 | Miyamoto |
| 7,517,572 B2 | 4/2009 | Van Dyke |
| 7,578,812 B2 | 8/2009 | Datta et al. |
| 7,658,813 B2 | 2/2010 | Petersen |
| 2006/0271004 A1 | 11/2006 | Petersen |
| 2007/0134489 A1 | 6/2007 | Neugebauer |
| 2011/0147475 A1 | 6/2011 | Biegler |
| 2011/0151171 A1 | 6/2011 | Biegler |

FOREIGN PATENT DOCUMENTS

| | | |
|---|---|---|
| EP | 0539032 | 4/1993 |
| EP | 0539504 | 5/1993 |
| EP | 0669121 | 8/1995 |
| EP | 0808145 | 11/1997 |
| JP | 11-181374 | 7/1999 |
| JP | 2000-14702 | 1/2000 |
| JP | 2002-45214 | 2/2002 |

OTHER PUBLICATIONS

International Search Report from International Application No. PCT/US2011/063682 dated Jun. 29, 2012.

US 5,389,416, 02/1995, Mody (withdrawn)

FASTENING TAB AND METHOD OF MAKING THE SAME

BACKGROUND

Mechanical fasteners, which are also called hook and loop fasteners, are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region.

Fastening tabs for the left and right portions of a diaper or incontinence garment can sometimes be prepared from a common continuous web, where a cut or cuts having a repeating pattern can be used to form nested pairs of fastening tabs. Such processes typically minimize waste during the manufacturing of fastening tabs. See, for example, U.S. Pat. No. 5,312,387 (Rossini et al.); U.S. Pat. No. 5,399,219 (Roessler et al.); and U.S. Pat. No. 7,371,302 (Miyamoto et al.); U.S. Pat. No. 7,658,813 (Petersen); and European Patent No. 0233704 B1, published Jul. 15, 1992.

Some fastening tabs have more than one region of mechanical fastener (e.g., hook patches) on the tab, which has been proposed to decrease the likelihood of unintentional disengagement of the mechanical fastener members. See, for example, U.S. Pat. No. 5,957,908 (Kline et al.) and U.S. Pat. No. 5,851,205 (Hisada et al.)

SUMMARY

Despite the progress in mechanical fastening technology, reliable mechanical fasteners and efficient methods of making them continue to be of interest. The present disclosure provides a fastening tab with multiple mechanical fastening patches and a method of making a plurality of such fastening tabs with minimal waste.

In one aspect, the present disclosure provides a fastening tab comprising:

a substrate comprising a main portion with a first distance (d1) between a top edge and an opposing bottom edge and a user's end portion extending from the main portion, the user's end portion having a top edge, an opposing bottom edge, and a side edge connecting the top edge and the opposing bottom edge, wherein a second distance (d2) between the top edge and the opposing bottom edge of the user's end portion is smaller than the first distance (d1);

a primary mechanical fastening patch having a side edge coterminous with the side edge of the user's end portion of the substrate, wherein the primary mechanical fastening patch has a third distance (d3) between a top edge and an opposing bottom edge, and wherein the third distance (d3) is smaller than the second distance (d2); and first and second auxiliary mechanical fastening patches on the main portion of the substrate, with the first auxiliary fastening patch coterminous with the top edge of the main portion of the substrate and the second auxiliary fastening patch coterminous with the opposing bottom edge of the main portion of the substrate, wherein each of the first and second auxiliary fastening patches has a height (d4a and d4b) between a top edge and a opposing bottom edge that is smaller than the third distance (d3). In some embodiments, the fastening tab is prepared or preparable by the method described below.

In another aspect, the present disclosure provides a method of making fastening tabs, the method comprising:

providing a substrate web extending in a machine direction;

attaching multiple discrete patches of mechanical fastener to the substrate web so that the multiple patches of mechanical fastener are separated in the machine direction; and cutting through the substrate web and the multiple patches of mechanical fastener in the machine direction with a continuous, meandering cut to provide two sub-webs, each sub-web having first and second cut portions of the multiple patches of mechanical fastener. In some embodiments, the method further comprises providing cross-web direction cuts through each sub-web to provide a plurality of fastening tabs, wherein the cross-web direction cuts cut through the second cut portions of the multiple patches of mechanical fastener.

In another aspect, the present disclosure provides a web comprising multiple fastening tabs, each according to the present disclosure and/or prepared according to the method disclosed herein, wherein the multiple fastening tabs are connected together at lines of weakness.

In another aspect, the present disclosure provides an absorbent article having at least a front waist region, a rear waist region, and a longitudinal center line bisecting the front waist region and the rear waist region, wherein at least one of the front waist region or the rear waist region comprises a fastening tab according to the present disclosure and/or prepared according to the method disclosed herein.

In another aspect, the present disclosure provides a web comprising:

a substrate web extending in a machine direction and having a cross-web direction and left and right longitudinal edges;

multiple discrete patches of mechanical fastener, separated in the machine direction, and attached to the substrate web; and a meandering line of weakness extending in the machine direction through each of the multiple discrete patches of mechanical fastener to form first and second cut portions from each of the multiple discrete patches of mechanical fastener.

The fastening tabs according to and/or made according to the present disclosure may provide robust engagement to complementary mechanical fastening patches due to, for example, the primary and first and second auxiliary mechanical fastening patches. Also, since the first and second auxiliary mechanical fastening patches are on the main portion of the fastening tab, while the primary mechanical fastening patch is on the user's end portion of the fastening tab, the fastening tabs according to and/or made according to the present disclosure may resist shifting forces such as torsional or rotational forces caused by movement of the wearer of the absorbent article.

The method of making fastening tabs according to the present disclosure can provide nested left and right fastening tabs for manufacturing of absorbent articles from the same web of material. The discrete mechanical fastening patches spaced apart on the web allow for the unique position of mechanical fastening patches, for example, on the fastening tabs disclosed herein.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second", "top" and "bottom", and "left" and "right" are used in this disclosure. It will be understood that, unless otherwise noted, those terms are used in their relative sense only. In particular, in some embodiments certain "first" and "second" components may be present in interchangeable and/or identical multiples (e.g., pairs). For these components, the designation of "first" and "second", "top" and "bottom", and "left" and "right" may be applied to the components merely as a matter of convenience in the description of one or more of the embodiments.

The term "machine direction" (MD) as used above and below denotes the direction of a running, continuous web of the substrate during the manufacturing of the fastening tab. As used herein, the terms machine direction and longitudinal direction are typically used interchangeably. The term "cross-direction" (CD) as used above and below denotes the direction which is essentially perpendicular to the machine direction.

The term "nonwoven" when referring to a substrate or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
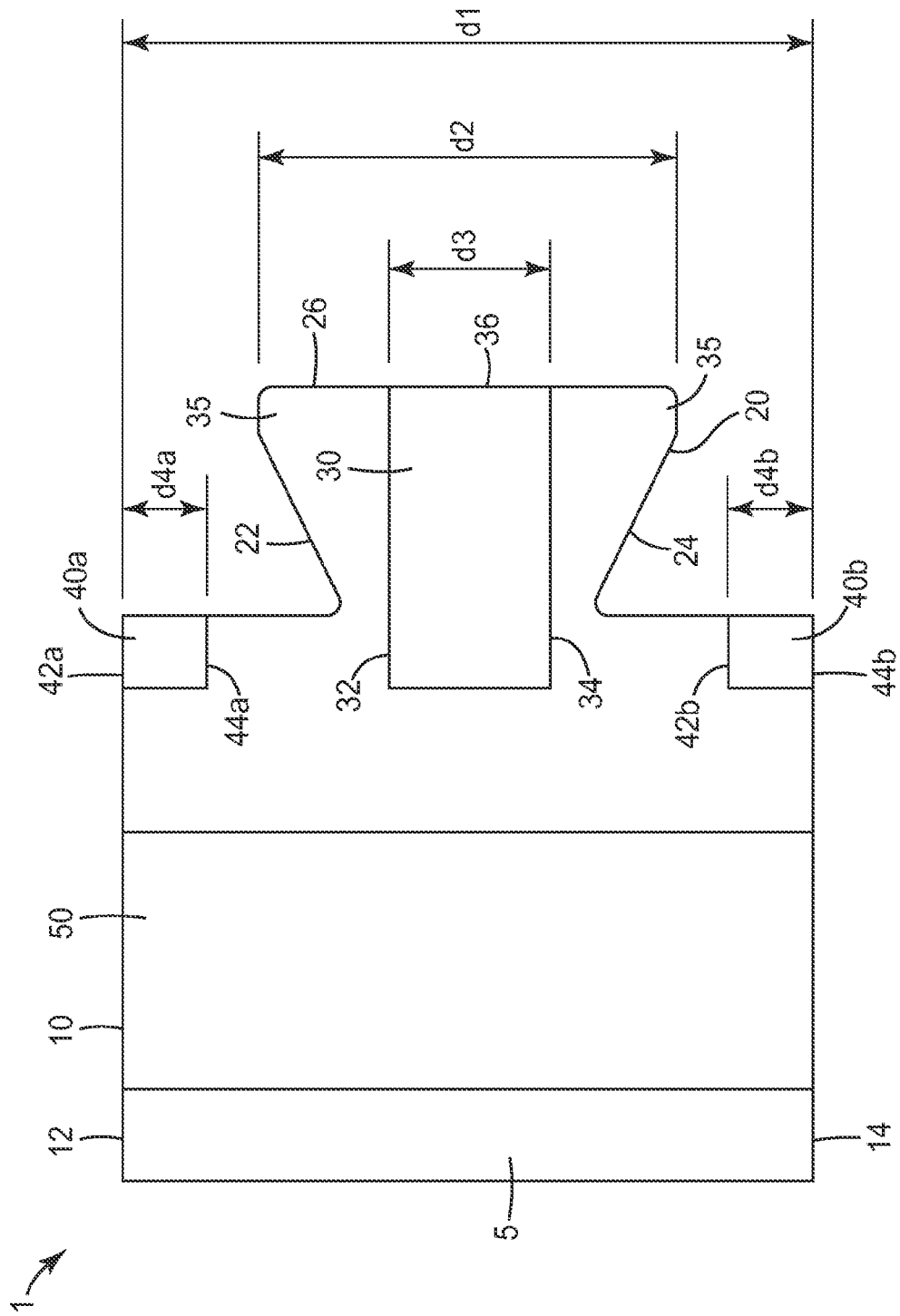
FIG. 1 is a schematic top view of an exemplary fastening tab according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

FIG. 1 illustrates a fastening tab 1 according to some embodiments of the present disclosure. Fastening tab 1 includes a substrate 5 having a main portion 10 and a user's end portion 20 extending from the main portion 10. Main portion 10 has a top edge 12 and an opposing bottom edge 14 with a first distance (d1) between top edge 12 and bottom edge 14. User's end portion 20 has a top edge 22, an opposing bottom edge 24, and a side edge 26 connecting top edge 22 and opposing bottom edge 24, with a second distance (d2) between top edge 22 and bottom edge 24. The second distance (d2), the height of the user's end portion, is smaller than the first distance (d1), the height of the main portion. When the top and bottom edges 12 and 14 of the main portion 10 are not parallel, the first distance (d1) is defined at the point of the greatest distance between the top edge 12 and the bottom edge 14 of the main portion 10. Similarly, when the top and bottom edges 22 and 24 of the user's end portion 20 are not parallel, as in the illustrated embodiment, the second distance (d2) is defined at the point of the greatest distance between the top edge 22 and the bottom edge 24 of the user's end portion 20.

Fastening tab 1 also includes a primary mechanical fastening patch 30 and first and second auxiliary mechanical fastening patches 40a and 40b, respectively. Primary mechanical fastening patch 30 has top and bottom edges 32 and 34 and a side edge 36 coterminous with the side edge 26 of the user's end portion of the substrate 5. Primary mechanical fastening patch 30 has a third distance (d3) between top edge 32 and opposing bottom edge 34 that is smaller than the second distance (d2) between the top and bottom edges 22 and 24 of the user's end portion 20, which is advantageous, for example, for providing at least one finger lift region 35 on the user's end portion 20. In some embodiments, including the illustrated embodiment, there are two finger lift regions 35. First and second auxiliary mechanical fastening patches 40a and 40b are located on the main portion 10 of the substrate 5. One auxiliary fastening patch 40a, the first auxiliary fastening patch, has a top edge 42a and a bottom edge 44a, with the top edge 42a coterminous with the top edge 12 of the main portion 10 of the substrate 5. One auxiliary fastening patch 40b, the second auxiliary fastening patch, has a top edge 42b and a bottom edge 44b, with the bottom edge 44b coterminous with the bottom edge 14 of the main portion 10 of the substrate 5. Each of the first and second auxiliary fastening patches 40a and 40b has a height (d4 and d4b) between a top edge 42a and 42b and an opposing bottom edge 44a and 44b that is smaller than the third distance (d3). In some embodiments, including the illustrated embodiment, the sum of the height of the first auxiliary fastening patch (d4a) and the height of the second auxiliary fastening patch (d4b) is equal to the third distance (d3). In some embodiments, (d4a) and (d4b) are each half or about half of (d3).

In the embodiment illustrated in FIG. 1, primary mechanical fastening patch 30 extends into the main portion 10 of the substrate 5, and primary mechanical fastening patch 30 and the first and second auxiliary mechanical fastening patches 40a and 40b are aligned in the main portion 10 of the substrate 5. That is, in the illustrated top view, the left edges of primary 30 and first and second auxiliary mechanical fastening patches 40a and 40b are aligned in the main portion 10. In other embodiments, as described in further detail below, the primary mechanical fastening patch is located only on the user's end portion 20, which means it does not extend into the main portion 10.

In the embodiment illustrated in FIG. 1, main portion 10 of substrate 5 exhibits the optional feature of a zone 50 that is extensible in at least one direction. The zone 50 of extensibility may be extensible in any direction, for example, at a non-zero angle to the longitudinal direction of the fastening tab. The longitudinal direction of the fastening tab is the direction in which arrow (d1) points in FIG. 1. In some embodiments, when the primary mechanical fastening patch 30 is separated from the first and second auxiliary mechanical fastening patches 40a and 40b in a first direction (e.g., the longitudinal direction of the fastening tab), the zone 50 is extensible in a direction perpendicular to the first direction. This arrangement allows the fastening tab to stretch when the user's end portion is grasped and attached to a complementary mechanical fastening surface of an absorbent article, for example. Further discussion of zones of a substrate, which in some embodiments are extensible zones, is provided below in connection with substrate web 105 in FIGS. 2A to 2D.

Figure 2A:
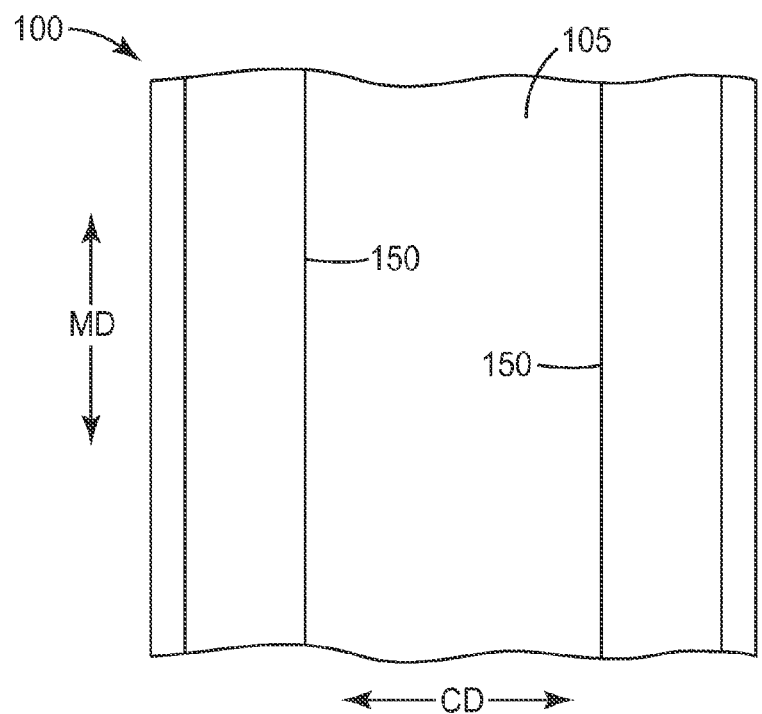
FIG. 2A schematically shows a top view of a substrate web with optional zones of extensibility, which is useful for some embodiments of the method of making fastening tabs and the web according to the present disclosure.

FIGS. 2A to 2D illustrate, for example, a web 100-103 in various stages of the method of making fastening tabs according to the present disclosure. FIG. 2A schematically shows a top view of web 100 having a machine direction (MD) and a cross-web direction (CD). Web 100 includes substrate web 105 with optional zones of extensibility 150, described in further detail below.

Figure 2B:
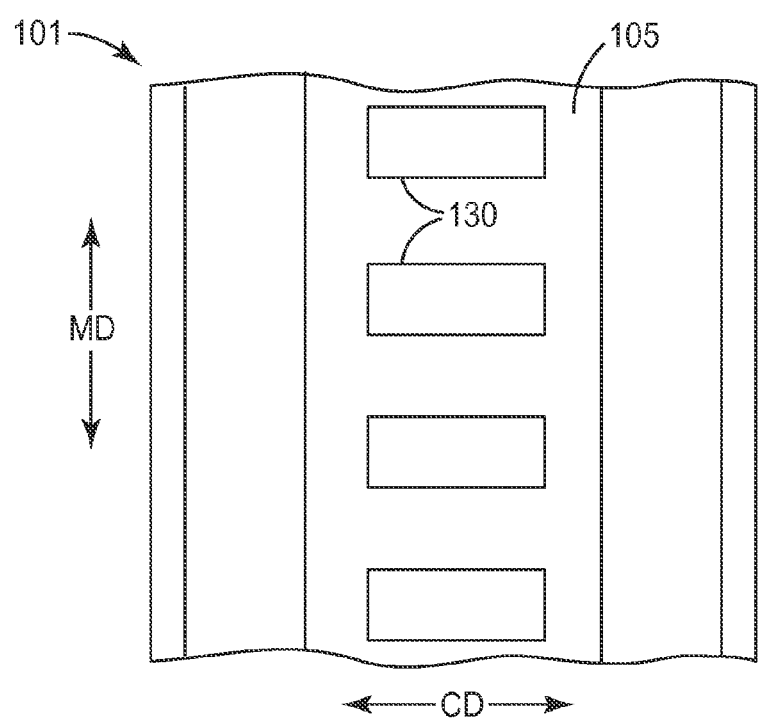
FIG. 2B schematically shows a top view of the substrate web of FIG. 2A with multiple discrete patches of mechanical fastener.

For web 101 in FIG. 2B, multiple discrete patches of mechanical fastener 130 are attached to the substrate web 105 so that the multiple patches of mechanical fastener 130 are separated in the machine direction. The multiple patches of mechanical fastener 130 may be joined to the substrate, for example, with adhesives (e.g., pressure sensitive adhesives or hot melt adhesives) or by other bonding methods (e.g., ultrasonic bonding, mechanical bonding such as compression bonding, or thermal bonding such as surface bonding). The surface opposite the mechanical fastening elements is attached to substrate web 105 so that the mechanical fastening elements are exposed. In the illustrated embodiment, the multiple discrete patches of mechanical fastener 130 are provided in a single row, centered on the substrate web 105, and the multiple discrete patches of mechanical fastener 130 are equivalent in size. The expression "equivalent in size" means that the multiple discrete patches of mechanical fastener each have a length within about 5, 2.5, or 1 percent the average length of the mechanical fastening patches and a width within about 5, 2.5, or 1 percent the average width of the mechanical fastening patches.

The multiple discrete patches of mechanical fastener 130 may be provided, for example, by continuously unwinding a supply roll from which discrete patches are cut and applied individually to the substrate web 105. After being cut from a supply roll, the discrete patches 130 may be fed, for example, into a lamination station where they are laminated to the substrate web 105. The discrete patches 130 can be held in place during lamination, for example, using a vacuum roller. It is also possible that the multiple discrete patches of mechanical fastener are provided in the form of discrete patches which are temporarily attached, for example, to an auxiliary web. The discrete patches of mechanical fastener 130 are then secured to the substrate web 105, and the auxiliary web is wound up.

Figure 2C:
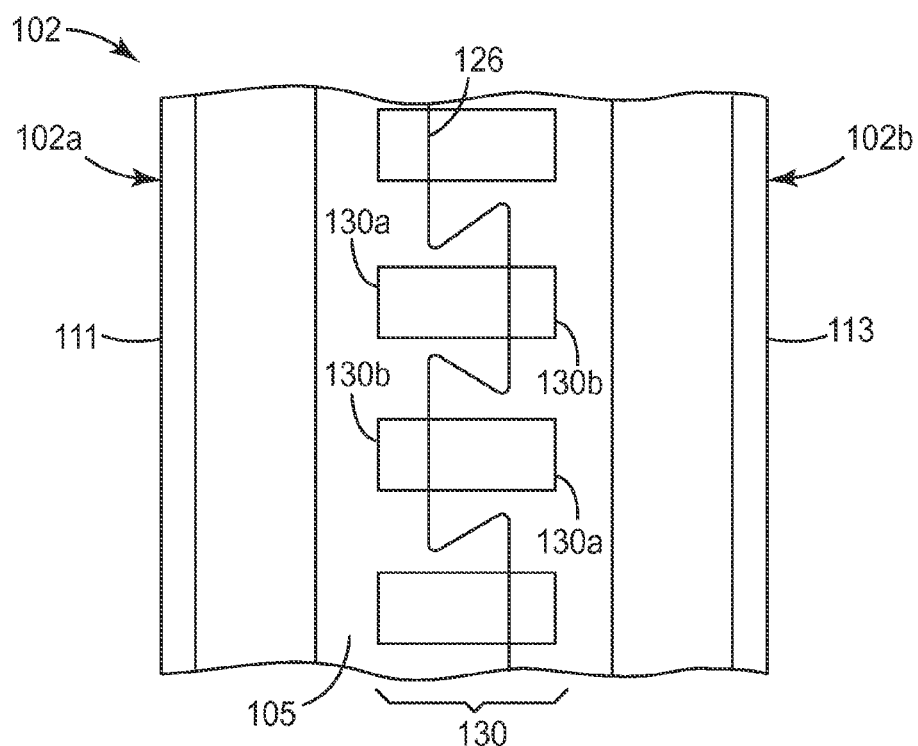
FIG. 2C schematically shows a top view of the web of FIG. 2B with a continuous, meandering cut through the substrate web and the discrete patches of mechanical fastener.

FIG. 2C schematically shows a top view of the web 101 of FIG. 2B with a continuous, meandering cut 126 through the substrate web 105 and the discrete patches of mechanical fastener 130. Continuous, meandering cut 126 provides two sub-webs 102a and 102b. Since continuous, meandering cut 126 cuts the substrate web 105 and the multiple patches of mechanical fastener 130, the two sub-webs 102a and 102b each have first 130a and second 130b cut portions of the multiple patches of mechanical fastener 130. Cut 126 is continuous in the machine direction between left and right longitudinal edges 111 and 113, which means cut 126 doesn't reach either longitudinal edge 111 or 113. In this sense, the term "continuous" does not exclude lines of perforation. The continuous cut may be a complete cut in the web 102 or it may be a line of perforation through the thickness of the web or other line of weakness (e.g., partial-depth cut or thinned portion of the web) that allows the sub-webs 102a and 102b to be separated. The continuous, meandering cut generally defines the shape of a user's end portion of each fastening tab prepared. FIG. 2C also illustrates an embodiment of a web according to the present disclosure. The web has multiple discrete patches of mechanical fastener 130 separated in the machine direction and attached to the substrate web 105 and a meandering line of weakness 126 extending in the machine direction through each of the multiple discrete patches of mechanical fastener 130.

Figure 2D:
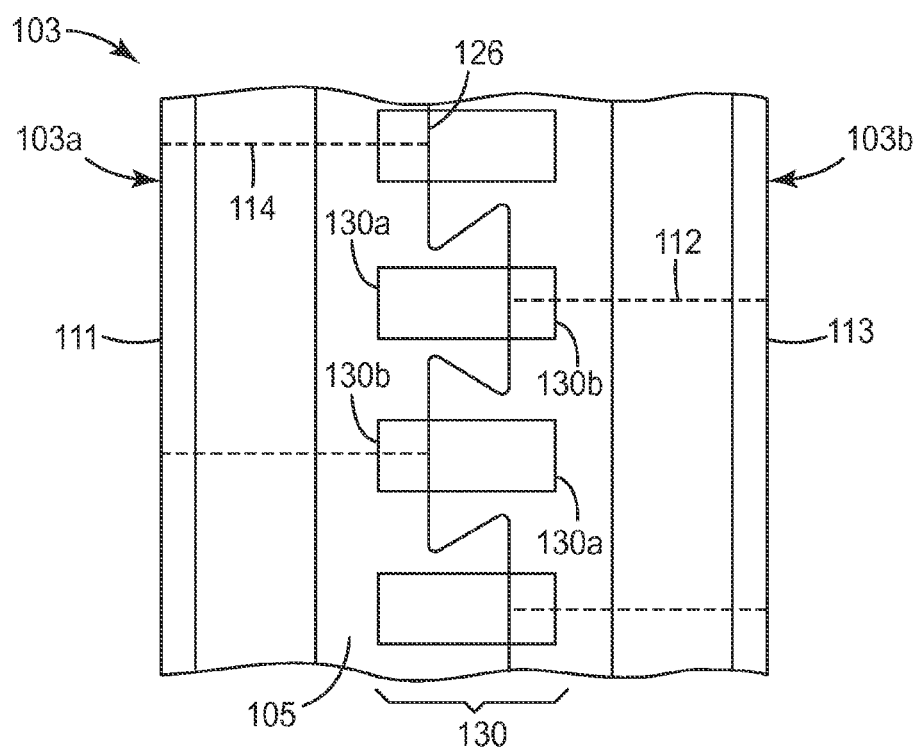
FIG. 2D schematically shows a top view of the web of FIG. 2C with cross-web direction cuts through each sub-web to provide a plurality of fastening tabs.

In some embodiments of the web and method of making fastening tabs according to the present disclosure, as depicted in FIGS. 2C and 2D, continuous, meandering cut 126 is centered on the substrate web 105. The continuous, meandering cut 126 typically has an undulating pattern. In the illustrated embodiment, cut 126 provides a series of nested trapezoidal shapes. Other shapes are possible as described below.

FIG. 2D schematically shows a top view of the sub-webs of FIG. 2C with cross-web direction cuts 112 and 114 through each sub-web 103a and 103b to provide a plurality of fastening tabs. Cross-web direction cuts 112 and 114 through each sub-web go from one of the left or right longitudinal edges 111 or 112 to the meandering cut 126 through the second cut portions 130b of the multiple patches of mechanical fastener 130. When the web 103 is viewed as a whole as in FIG. 2D, the cross-web direction cuts 112 and 114 are generally multiple, staggered cuts extending alternately from the left and right longitudinal edges 112 and 114 to the continuous, meandering cut 126 through second cut portions 130b of successive multiple discrete patches of mechanical fastener 130. The cross-web direction cuts 112 and 114 generally do not cut through the first cut portions 130a but terminate at the meandering cut 126. Each fastening tab thus formed has three mechanical fastening regions: a first cut portion 130a from one patch of mechanical fastener and a part of a second cut portion 130b from each adjacent patch of mechanical fastener.

The cross-web-direction cuts may be complete cuts in the sub-web 103a and 103b or they may be a lines of perforation or other lines of weakness that allow individual fastening tabs to be separated from each other. FIG. 2D also illustrates embodiments of webs comprising multiple fastening tabs according to the present disclosure. In some embodiments of the web according to the present disclosure, in addition to the meandering line of weakness (e.g., perforation or partial-depth cut) 126, web 103 may also have multiple, staggered lines of weakness (e.g., perforations or partial-depth cuts) 112 and 114 extending alternately from the left and right longitudinal edges 111 and 113 to the meandering line of weakness 126, the multiple, staggered lines of weakness 111 and 113 extending through successive multiple discrete patches of mechanical fastener 130. In some embodiments of a web according to the present disclosure comprising multiple fastening tabs, the multiple fastening tabs are connected together at lines of weakness (e.g., perforations or partial-depth cuts). In FIG. 2D, each sub-web 103a and 103b represents an exemplary web comprising multiple fastening tabs according to the present disclosure. Each sub-web 103a and 103b may be individually wound into a roll for later separation of the fastening tabs.

Cutting the web 102 or 103 with the continuous, meandering cut 126 and/or the cross-web direction cuts 112 and 113 may be performed by using a variety of methods, for example, rotary cutters, air knives, thermal knives, pinch cutters, ultrasonic cutters, laser cutters, or a combination thereof. In some embodiments, the two sub-webs 102a and 102b are separated before providing the cross-web direction cuts. Each sub-web 102a and 102b may be individually wound into a roll before cross-web direction cuts 112 and 114 are applied.

FIGS. 3 through 6 schematically show top views of exemplary webs according to the present disclosure and/or webs made according to some embodiments of the method disclosed herein. In each of FIGS. 3 to 6, web 203, 303, 403, and 503 has a substrate web 105 with multiple discrete patches of mechanical fastener 130 and 230 separated in the machine direction and attached to the substrate web. Each web 105 has a meandering cut 226, 326, 426, and 526, continuous in the machine direction, dividing each web into two sub-webs. Cross-web direction cuts 112 and 114 through each sub-web go from one of the left or right longitudinal edges 111 or 113 to the meandering cut 226, 326, 426, and 526 through the second cut portions 130b or 230b of the multiple patches of mechanical fastener 130. In the illustrated embodiments, the substrate web has at least two extensible zones 150 that extend in the machine direction, the extensible zones being extensible in at least a direction at a non-zero angle to the machine direction. In each of FIGS. 3 to 6, the continuous, meandering cut generally defines the shape of a user's end portion of each fastening tab prepared.

Figure 3:
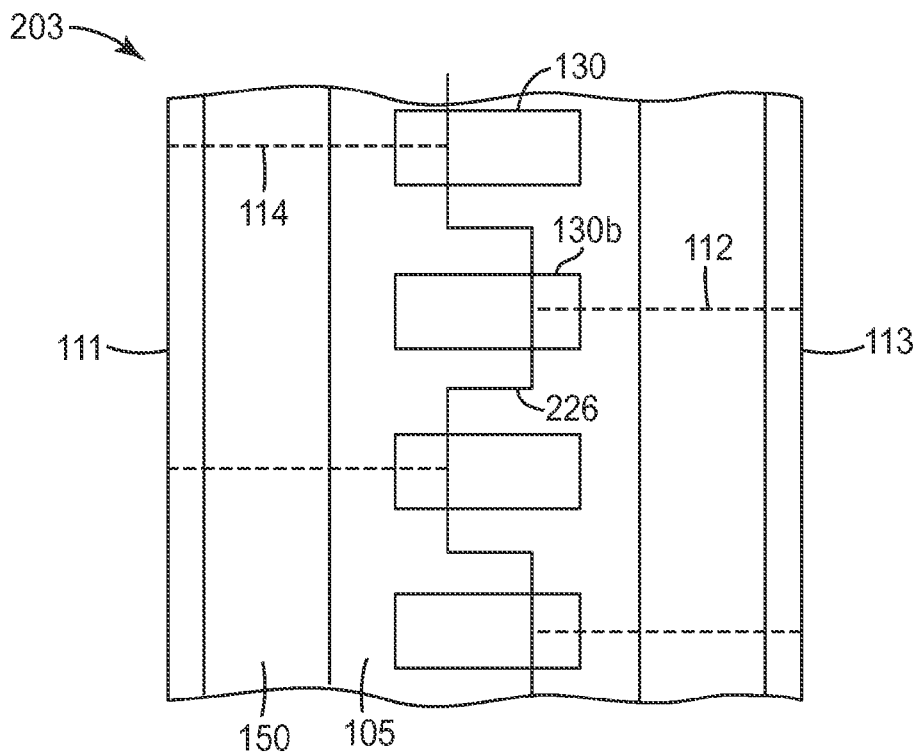
FIGS. 3 through 6 schematically show top views of exemplary webs with multiple discrete patches of mechanical fastener according to and/or made according to the present disclosure, the exemplary webs having various continuous, meandering cuts and various shapes of patches of mechanical fastener.

In FIG. 3, the continuous, meandering cut 226 has a regular pattern, which is a square wave pattern. The shape of a user's end portion of each fastening tab prepared in the illustrated embodiment is a rectangular shape.

Figure 4:
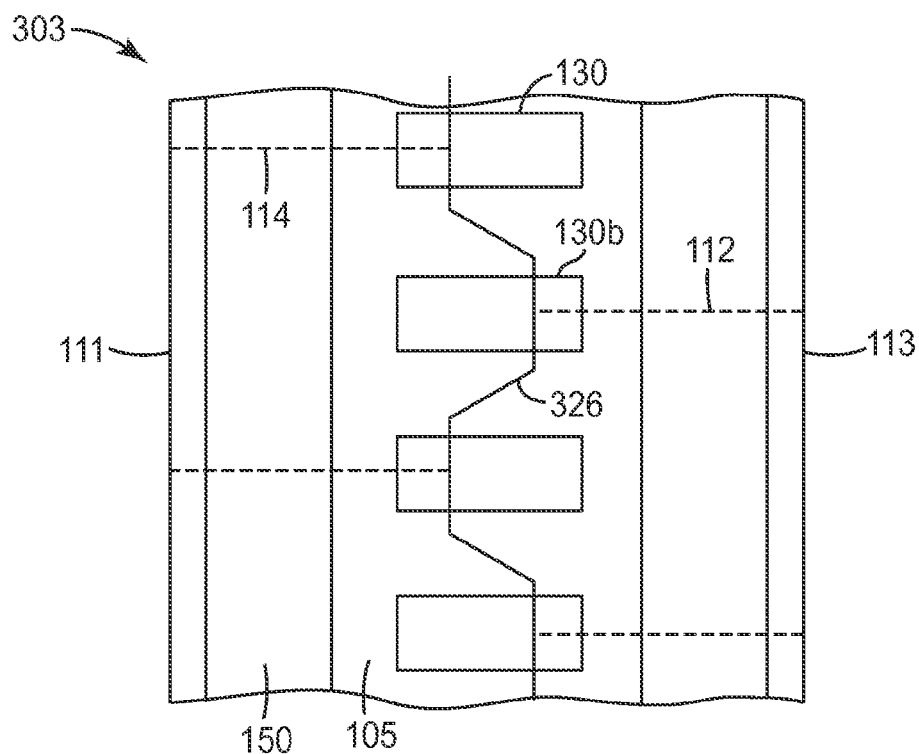

In FIG. 4, like the embodiment illustrated in FIGS. 2C and 2D, the continuous, meandering cut 326 has a regular pattern that provides a series of nested trapezoidal shapes. In the embodiment shown in FIG. 4, the fastening tab is narrower at the side edge of the user's end portion than at the junction with the main portion, while in FIGS. 2C and 2D, the fastening tab is wider at the side edge 26 of the user's end portion than at the junction with the main portion.

Figure 5:
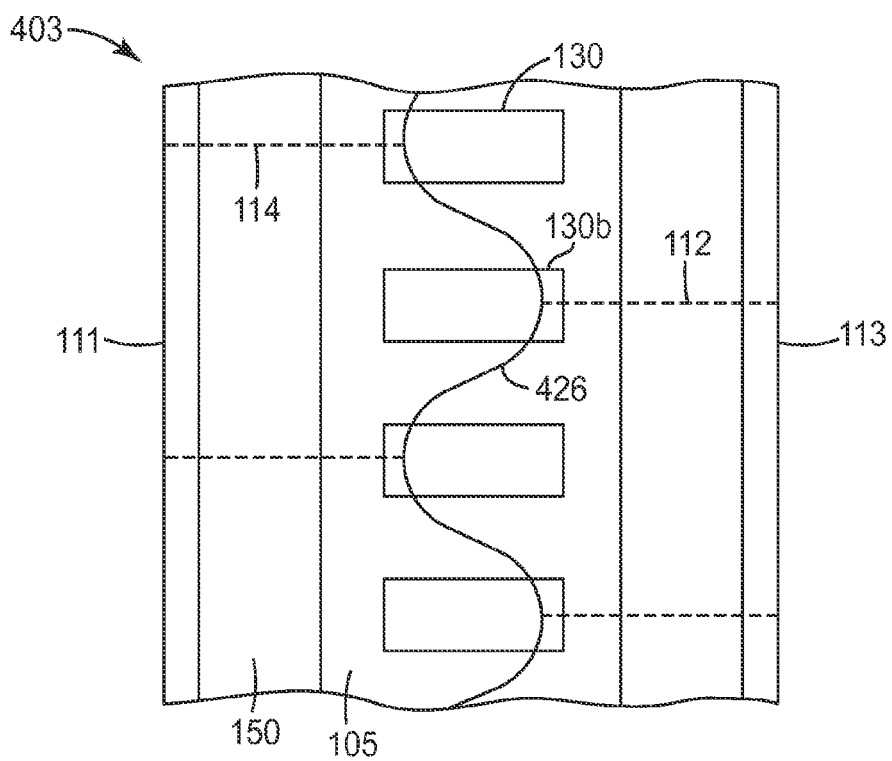

In FIG. 5, the continuous, meandering cut 426 has a regular pattern, which is sinusoidal. The shape of a user's end portion of each fastening tab prepared in the illustrated embodiment is a curved shape.

Figure 6:
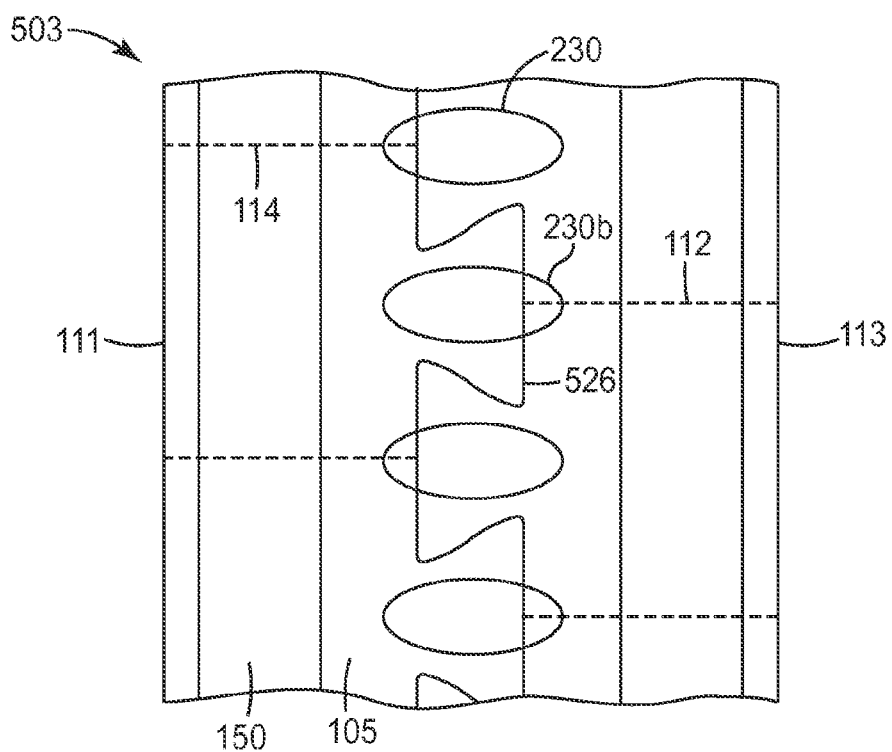

In FIG. 6, like the embodiment illustrated in FIGS. 2C and 2D, the continuous, meandering cut 526 has a regular pattern that provides a series of nested trapezoidal shapes. The shape of the user's end portion of each fastening tab prepared in the illustrated embodiment is the same as that of FIGS. 2C and 2D; however, each of the multiple mechanical fastening patches 230 in FIG. 6 is oval in shape.

Other shapes of mechanical fastening patches may be useful for practicing the present disclosure. Typically, the mechanical fastening patches have an elongated shape; that is, the mechanical fastening patch is longer in one direction than the other. The longer sides are aligned generally with the cross-web direction. In some embodiments, the mechanical fastening patches are in the shape of an hourglass. Similarly, the continuous, meandering cut may have any suitable repeating pattern to form fastening tabs having a variety of shapes. For example, the continuous, meandering cut can provide a fastening tab having a user's end with a shape like any of the shapes shown in FIGS. 1 and 3-7 of U.S. Pat. No. 5,312,387 (Rossini et al.); FIG. 4C of U.S. Pat. No. 5,399,219 (Roessler et al.); FIGS. 4 and 6 to 9 of U.S. Pat. No. 7,371,302 (Miyamoto et al.); and FIGS. 3, 4, and 6 of European Patent No. 0233704 B1, published Jul. 15, 1992. In some embodiments, the fastening tab is narrower at the side edge of the user's end portion than at the junction with the main portion, and in other embodiments, the fastening tab is wider at the side edge of the user's end portion than at the junction with the main portion. In general, each tab has mirror symmetry about a central axis, and adjacent tabs on each sub-web are identical. Also, generally, each tab one sub-web (e.g., sub-web 103a in FIG. 2D) has a mirror image on the other sub-web (e.g., sub-web 103b in FIG. 2D), which is useful, for example, for manufacturing both left and right fastening tabs for an absorbent article from the same web of material.

Figure 7:
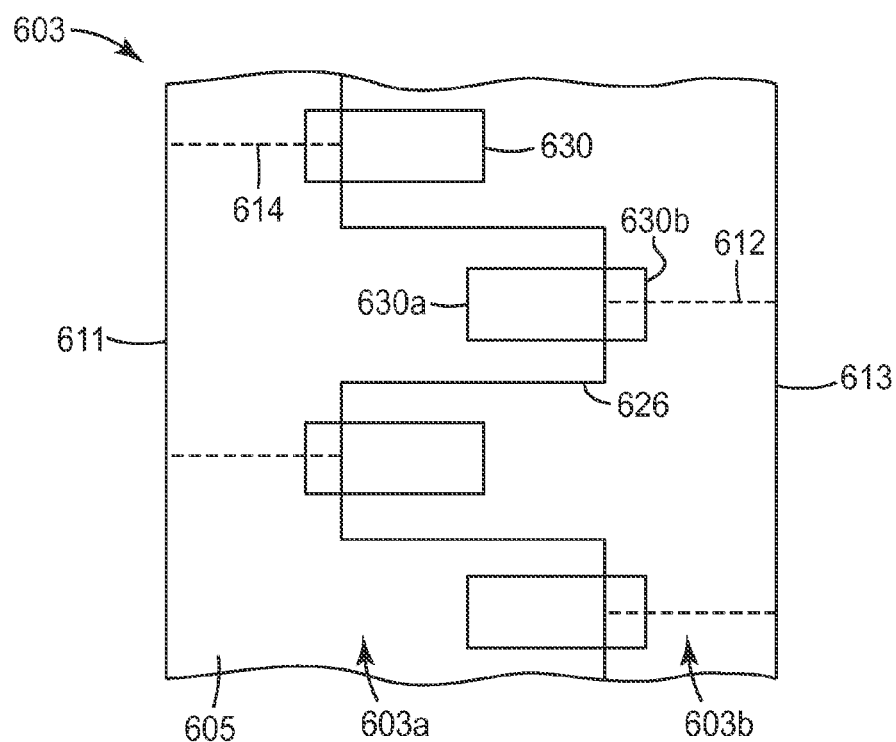
FIG. 7 schematically shows a top view of another embodiment of exemplary web with multiple discrete patches of mechanical fastener according to and/or made according to the present disclosure, the exemplary web having multiple patches of mechanical fastener in a staggered configuration.

FIG. 7 schematically shows a top view of another embodiment of a web according to the present disclosure and/or a web made according to another embodiment of the method disclosed herein. In FIG. 7, web 603 has a substrate web 605 with multiple discrete patches of mechanical fastener 630 separated in the machine direction and attached to the substrate web. Web 605 has a meandering cut 626, continuous in the machine direction, dividing web 603 into two sub-webs 603a and 603b. Cross-web direction cuts 612 and 614 through each sub-web go from one of the left or right longitudinal edges 611 or 613 to the meandering cut 626 through the second cut portions 630b of the multiple patches of mechanical fastener 630 (and not through the first cut portions 630a). In the illustrated embodiments, multiple patches of mechanical fastener 630 are positioned in a staggered configuration. The multiple discrete patches of mechanical fastener 630 are staggered in the cross-web direction in a central portion of the substrate web 605. That is, half of the mechanical fastening patches are closer to the left longitudinal edge 611 than the right longitudinal edge 613, and half of the mechanical fastening patches are closer to the right longitudinal edge 613 than the left longitudinal edge 611. In this embodiment, the fastening tabs that are provided after cross-web direction cuts 612 and 614 are made have first cut portions 630a that do not extend onto the main portion of the substrate. The portions of second cut portions 630b and the first cut portion 630a are not aligned with each other. Any of the shapes of mechanical fastening patches and meandering cuts described above may be useful with this embodiment.

The substrate 5 in FIG. 1 or substrate web 105 and 605 in FIGS. 2 through 7, useful for fastening tabs, webs, and methods according to the present disclosure, may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the substrate is a fibrous material (e.g., a woven, nonwoven, or knit material). In some embodiments, the substrate comprises multiple layers of nonwoven materials with, for example, at least one layer of a meltblown nonwoven and at least one layer of a spunbonded nonwoven, or any other suitable combination of nonwoven materials. For example, the substrate may be a spunbond-meltbond-spunbond, spunbond-spunbond, or spunbond-spunbond-spunbond multilayer material. Or, the substrate may be a composite web comprising a nonwoven layer and a dense film layer. The substrate may be continuous (i.e., without any through-penetrating holes) or discontinuous (e.g. comprising through-penetrating perforations or pores).

Fibrous materials that provide useful substrates 5 and substrate webs 105 and 605 may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multicomponent fibers, for example, having a core of one thermoplastic material and a sheath of another thermoplastic material.

Useful substrates 5 and substrate webs 105 and 605 may have any suitable basis weight or thickness that is desired for a particular application. For a fibrous substrate or substrate web, the basis weight may range, for example, from at least about 20, 30, or 40 grams per square meter, up to about 400, 200, or 100 grams per square meter. The substrate or substrate web may be up to about 5 mm, about 2 mm, or about 1 mm in thickness and/or at least about 0.1, about 0.2, or about 0.5 mm in thickness.

The substrate 5 or substrate web 105 and 605 may comprise only one material and exhibit a uniform construction in the cross direction. In some embodiments, the substrate web exhibits a sequence of two or more zones having different properties in cross direction, with such zones typically extending continuously in the machine direction. The term "zone" as used above and below refers to a section of the substrate 5 or substrate web 105 or 605 exhibiting an essentially uniform construction and/or uniform properties. The different zones can be formed by different materials which are joined to each other, for example, by adhesive means (e.g., pressure-sensitive adhesives), ultrasonic bonding, thermal bonding, mechanical bonding, stitching, or any combination of these bonding methods. It is also possible that different zones are created by "activating" one or more zones of the substrate web, for example, by subjecting the substrate web 105 and 605 to a mechanical, thermal, electrical, and/or chemical treatment in order to impart different functionalities to the treated zones of the substrate web. Different zones may consist essentially of one material, but it is also possible that the zones comprise a sequence of two or more layers of materials and/or exhibit substructures in the direction normal to the major surfaces of the substrate web.

In some embodiments of a fastening tab according to the present disclosure, the main portion 10 of the substrate 5 has a zone that is extensible in at least one direction. Useful extensible materials may have any percentage of elongation, as desired. In some embodiments of the web and the method of making fastening tabs according to the present disclosure, the substrate web 105 and 605 has at least two extensible zones that run in the machine direction, the extensible zones being extensible at least in a direction at a non-zero angle to the machine direction. In some embodiments, the extensible zones are made from elastically extensible materials that extend in at least one direction when a force is applied and return to approximately their original dimension after the force is removed. However, in some embodiments, at least the portion of the substrate joined to the multiple discrete patches of mechanical fastener 130 is not elastically extensible (that is, nonelastic). The term "elastic" refers to any material that exhibits recovery from stretching or deformation. Likewise, the term "nonelastic" refers to any material that does not exhibit recovery from stretching or deformation.

Elastically extensible materials which are useful for practicing the present disclosure include materials which are elastically extensible without requiring an activation step. Such materials include elastic, natural or synthetic rubber, rubber foams, elastomeric scrims, woven or non-woven elastomeric webs, elastomeric composites, zero-strain stretch laminates, and prestrained stretch laminates. The elastically extensible materials may be made from a group of materials comprising essentially isotropic or essentially anisotropic materials. Useful elastic materials preferably exhibit an elongation at break as measured according to ASTM D 882 in the direction of stretchability of at least 25%, at least 50%, and in some embodiments at least 100%. "Elongation" in terms of percent refers to [(the extended length−the initial length)/the initial length] multiplied by 100.

Suitable essentially isotropically elastic materials include elastomeric polyurethane materials, natural or synthetic rubber materials (e.g., ethylene-propylene-diene (EPDM) copolymers, styrene-butadiene-styrene block (SBS) copolymers, styrene-(ethylene-butylene)-styrene block (SEBS) copolymers, and other thermoplastic elastomers such as AB and ABA block copolymers), elastomeric polyamide materials, elastomeric polyolefin materials, and elastomeric polyester materials. Blends of these elastomers with each other or with modifying non-elastomers are also contemplated.

Many types of thermoplastic elastomers are commercially available, including those from BASF under the trade designation "STYROFLEX", from Shell Chemicals under the trade designation "KRATON", from Dow Chemical under the trade designation "PELLETHANE" or "ENGAGE", from DSM under the trade designation "ARNITEL", from DuPont under the trade designation "HYTREL", from Exxon Mobil Corp. under the trademark "VECTOR", and more.

In some embodiments, elastically extensible zones are incorporated into substrate web 105 using an activation treatment, for example, to render such zones elastically extensible and/or to increase such elastic extensibility. Suitable activation treatments include ring rolling, embossing, thermoforming, high pressure hydraulic forming, and casting. Elastomeric laminates comprising at least one non-elastomeric skin layer and at least one core layer where the laminate is treated to exhibit preferential activation regions and non-preferential activation regions so that the preferential activation regions can be stretched to an elastic state, are disclosed, for example, in U.S. Pat. No. 5,344,691 (Hanschen et al.).

Web 100 to 103 and 203-603 may comprise further materials such as stiffening materials, adhesive coatings, release materials (e.g., release coatings and release tapes), colored films, printings, or registered marks. Stiffening materials include thermally or sonically structured surfaces and additional layers or coatings applied to the substrate web 105 or 605. In some embodiments, one or more zones of the substrate web 105 or 605 comprises a backing or carrier film in order to impart structural integrity and/or stiffness to the substrate web 105 or 605 in the cross direction. The backing or carrier film may be selected from a variety of films or sheetings including single- or multilayered films, coextruded films, laterally laminated films or films comprising foam layers. The layers of such films or sheetings may comprise various materials such as polypropylene, polyvinylchloride, polyethylene terepthalate, polyethylene, polyolefin copolymers or blends of polyolefins such as, for example, a blend of polypropylene, LPDE (low density polyethylene) and/or LLDPE (linear low density polyethylene), textiles, and non-woven and foamed materials. The thickness of the backing can be between 30 and 500 µm, in some embodiments between 40 and 150 µm. The basis weight of the backing can be between 20 and 500 g/m$^2$, in some embodiments between 40 and 300 g/m$^2$ or between 40 and 200 g/m$^2$.

In some embodiments of the fastening tab according to the present disclosure, the primary and first and second auxiliary mechanical fastening patches are loop patches. In some embodiments of the webs and/or method of making fastening tabs according to the present disclosure, the multiple discrete patches of mechanical fastener are loop patches. Loop patches can be made from any suitable material that interlocks with corresponding hook fastening elements. In some embodiments, the loop fastening elements are typically formed from knitted, woven, or non-woven fabrics. For example, the mechanical fastening patches may include fiber loops projecting from a knitted, woven, or non-woven backing or may be extrusion-bonded, adhesive-bonded, and/or sonically-bonded fiber loops. Suitable commercially available mechanical fastening patches include knitted and extrusion-bonded loop materials from 3M Company, St. Paul, Minn.

In some embodiments of the fastening tab according to the present disclosure, the primary and first and second auxiliary mechanical fastening patches are hook patches. In some embodiments of the webs and/or method of making fastening tabs according to the present disclosure, the multiple discrete patches of mechanical fastener are hook patches. Hook patches useful for practicing the present disclosure typically have a backing and hook elements that are integral (that is, formed at the same time as a unit, unitary). Hook elements on a backing can be made by conventional extrusion through a die and cast molding techniques, for example, by feeding a thermoplastic material onto a continuously moving mold surface with cavities having the inverse shape of the hook elements. The thermoplastic material can be passed between a nip formed by two rolls or a nip between a die face and roll surface, with at least one of the rolls having the cavities. The cavities may be in the inverse shape of a hook element having a loop-engaging head or may be in the inverse shape of a stem or of a partially formed hook element (e.g., a precursor to a hook element). In the methods disclosed herein, the term "hook element" is meant to include stems without heads. Pressure provided by the nip forces the resin into the cavities. In some embodiments, a vacuum can be used to evacuate the cavities for easier filling of the cavities. The nip is typically sufficiently wide such that a coherent backing is formed over the cavities. The mold surface and cavities can optionally be air or water cooled before stripping the integrally formed backing and upstanding hook elements from the mold surface such as by a stripper roll. If the hook elements formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Another useful method for forming hook elements on a backing is profile extrusion described, for example, in U.S. Pat. No. 4,894,060 (Nestegard). Typically, in this method a thermoplastic flow stream is passed through a patterned die lip (e.g., cut by electron discharge machining) to form a web having downweb ridges, slicing the ridges, and stretching the web to form separated projections. The ridges may form hook precursors and exhibit the cross-sectional shape of hook elements (e.g., with loop-engaging heads) to be formed. The ridges are transversely sliced at spaced locations along the extension of the ridges to form discrete portions of the ridges having lengths in the direction of the ridges essentially corresponding to the length of the hook elements to be formed.

Generally, hook elements with loop-engaging heads have a head shape that is different from the shape of the stem. The term "loop-engaging" as used herein relates to the ability of a hook element to be mechanically attached to a loop material. For example, the hook element may be in the shape of a mushroom (e.g., with a circular or oval head enlarged with respect to the stem), a hook, a palm-tree, a nail, a T, or a J. The loop-engageability of hook elements may be determined and defined by using standard woven, nonwoven, or knit materials. A region of hook elements with loop-engaging heads generally will provide, in combination with a loop material, at least one of a higher peel strength, higher dynamic shear strength, or higher dynamic friction than a region of stems without loop-engaging heads. Typically, hook elements that have loop-engaging heads have a maximum thickness dimension of up to about 1 (in some embodiments, 0.9, 0.8, 0.7, 0.6, 0.5, or 0.45) millimeter.

Suitable thermoplastic materials for hook patches useful for practicing the present disclosure include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, a hook patch is made of a polyolefin (e.g., polyethylene, polypropylene, polybutylene, ethylene copolymers, propylene copolymers, butylene copolymers, and copolymers and blends of these materials).

In hook patches useful for practicing the present disclosure in any of its various embodiments, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments, the hook elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the hook elements have aspect ratio (that is, a ratio of height to width at the widest point) of at least about 2:1, 3:1, or 4:1.

Some hook patches useful as primary and first and second auxiliary mechanical fastening patches and discrete patches of mechanical fastener useful for practicing the present disclosure are commercially available, e.g., from 3M Company under the trade designations "CS-600" or "CS-1010".

In some embodiments of the method of making fastening tabs according to the present disclosure, where the substrate web is a fibrous web and the multiple discrete patches of mechanical fastener (e.g., hook patches) have a thermoplastic backing, attaching the discrete patches of mechanical fastener to the fibrous substrate web comprises impinging heated gaseous fluid (e.g., ambient air, dehumidified air, nitrogen, an inert gas, or other gas mixture) onto a first surface of the fibrous web while it is moving; impinging heated fluid onto the thermoplastic backing on the surface opposite the mechanical fastener elements; and contacting the first surface of the fibrous web with the backing so that the first surface of the fibrous web is melt-bonded (e.g., surface-bonded or bonded with a loft-retaining bond) to the surface of the backing opposite the mechanical fastening elements. Impinging heated gaseous fluid onto the first surface of the fibrous web and impinging heated gaseous fluid on the backing may be carried out sequentially or simultaneously. The term "surface-bonded" when referring to the bonding of fibrous materials means that parts of fiber surfaces of at least portions of fibers are melt-bonded to the backing, in such a manner as to substantially preserve the original (pre-bonded) shape of the backing, and to substantially preserve at least some portions of the surface of the backing in an exposed condition, in the surface-bonded area. Quantitatively, surface-bonded fibers may be distinguished from embedded fibers in that at least about 65% of the surface area of the surface-bonded fiber is visible above the surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

Melt-bonding (e.g., surface-bonding or loft-retaining bonding) using heated gaseous fluid may be carried out, for example, by passing a fibrous substrate web and the patches cut from a supply roll of mechanical fastener through a nip formed by two backing rolls. Methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.), incorporated herein by reference in their entirety.

The fastening tabs disclosed herein are useful, for example, in absorbent articles. Absorbent articles include diapers and adult incontinence articles, for example. Absorbent articles according to the present disclosure have at least a front waist region, a rear waist region, and a longitudinal center line bisecting the front waist region and the rear waist region, wherein at least one of the front waist region or the rear waist region comprises the fastening tab disclosed herein. The fastening tab may be bonded to at least one of the front waist region or the rear waist region extending outwardly from at least one of the left longitudinal edge or the right longitudinal edge of the absorbent article.

Figure 8:
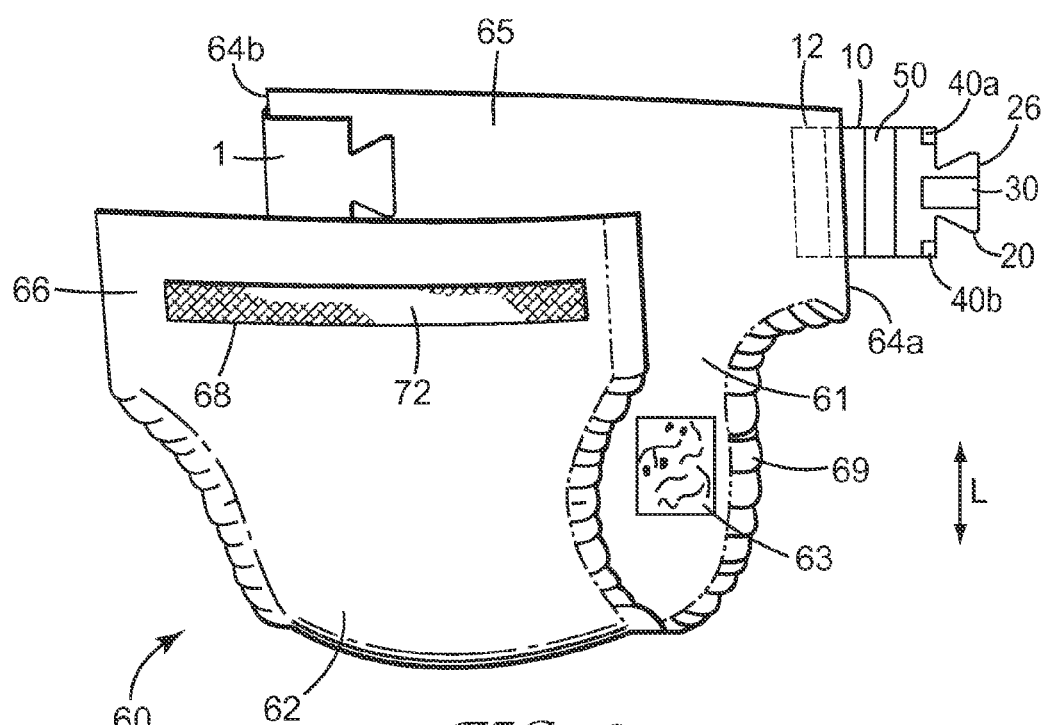
FIG. 8 is a perspective view of an absorbent article incorporating a fastening according to and/or made according to the present disclosure.

FIG. 8 is a schematic perspective view of a specific embodiment of an absorbent article according to the present disclosure. The absorbent article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 1 arranged at the two longitudinal edges 64a, 64b of diaper 60. The diaper 60 may comprise an elastic material 69 along at least a portion of longitudinal side edges 64a and 64b to provide leg cuffs. The longitudinal direction "L" of the absorbent article (e.g., diaper 60) refers to the direction that the article extends from the front to rear of the user. Therefore, the longitudinal direction refers to the length of the absorbent article between the rear waist region 65 and the front waist region 66. The lateral direction of the absorbent article (e.g., diaper 60) refers to the direction that the article extends from the left side to the right side (or vice versa) of the user (i.e., from longitudinal edge 64a to longitudinal edge 64b in the embodiment of FIG. 8). The top edge 12 of the main portion 10 of the fastening tab 1 is typically at an angle to the longitudinal direction of the absorbent article. The angle may be, for example, in a range from 30 to 90 degrees, 50 to 90 degrees, 60 to 90 degrees, 75 to 90 degrees, 80 to 90 degrees, or 85 to 90 degrees.

In FIG. 8, fastening tabs 1 are secured through their main portion 10 to the rear waist region 65. The user's end 20 of the fastening tab extends away from the rear waist region 65. The top edge 12 of the main portion 10 of the fastening tab 1 is typically at an angle to the longitudinal direction of the absorbent article. The angle may be, for example, in a range from 30 to 90 degrees, 50 to 90 degrees, 60 to 90 degrees, 75 to 90 degrees, 80 to 90 degrees, or 85 to 90 degrees. The configuration of fastening tab 1 illustrated in FIG. 8 is the same as that shown in FIG. 1, where there is a primary mechanical fastening patch 30 and first and second auxiliary mechanical fastening patches 40a and 40b. However, the fastening tab 10 may also be made from the webs shown in any of FIG. 2D or 3 to 7. In some embodiments, when attaching the diaper 60 to a wearer's body, the user's ends 20 of fastening tabs 1 can be attached to a target area 68 comprising fibrous material 72 which may be arranged on the back sheet 62 of the front waist region 66. Examples of loop tapes which may be applied to the target area 68 to provide an exposed fibrous material 72, are disclosed, for example, in U.S. Pat. No. 5,389,416 (Mody et al.) EP 0,341,993 (Gorman et al.) and EP 0,539,504 (Becker et al.). In other embodiments, the back sheet 62 comprises a woven or nonwoven fibrous layer which is capable of interacting with the primary mechanical fastening patch 30 and first and second mechanical fastening patches 40a and 40b. Examples of such back sheets 62 are disclosed, for example, in U.S. Pat. No. 6,190,758 (Stopper) and U.S. Pat. No. 6,075,179 (McCormack et al.).

There are numerous advantages of the fastening tab according to and/or made according to the present disclosure when it is incorporated into an absorbent article such as diaper 60 described above. For example, even if one of the spaced apart fastening patches, (e.g., the primary fastening patch 30) is unintentionally disengaged from the target area 68 or back sheet 62, the other mechanical fastening patches (e.g., the first and second auxiliary mechanical fastening patches 40a and 40b) are available to maintain the closure of the absorbent article. The mechanical engagement of the fastening tab is enhanced by the multiple patches of mechanical fastener, and the peel off of one of the primary or first or second auxiliary mechanical fastening patches does not cause the diaper to open up. Furthermore, with the multiple patches of mechanical fastener disclosed herein, adequate fastening between the primary and first and second auxiliary mechanical fastening patches 30, 40a, and 40b and the back sheet 62 may be possible, allowing the use of a smaller target area 68 or the elimination of target area 68 altogether, which offers material cost savings. For example, the target area may be designed so that only the primary mechanical fastening patch 30 engages with the target area 68. The first and second auxiliary fastening patches 40a and 40b, spaced apart from the primary mechanical fastener patch 30 in the longitudinal direction, may engage with the backsheet 62 on either side of the fastening patch.

Further advantages are associated with the configuration, for example, of the fastening tab according to and/or made according to the present disclosure. In use, fitting an absorbent article such as a diaper about the wearer usually requires the front and back waist portions of the diaper to overlap each other. As the diaper is worn the movements of the wearer tend to cause the overlapping front and back waist portions to shift position relative to each other. In other words, overlapping front and back waist portions are subjected to forces which tend to cause the front and back waist portions to assume a position relative to each other which is different from the position they assume when the diaper is initially fitted to the wearer. Such shifting can be made worse by the forces induced by the elastic at the leg openings. Unless such shifting is limited, the fit and containment characteristics of the diaper are degraded as the diaper is worn. The multiple mechanical fastening patches provided in the fastening tabs according to and/or made according to the present disclosure may provide improved fit and closure stability by resisting such shifting. The resistance to shifting may be enhanced because the primary mechanical fastening patches and the first and second auxiliary mechanical fastening patches are at different positions around the waist of the user. Referring again to FIG. 8, the first and second auxiliary mechanical fastening patches 40a and 40b on the main portion 10 of the fastening tab 1 are further back on the user's waist, while the primary mechanical fastening patch 30 is on the user's end portion 20 of the fastening tab 1, coterminous with side edge 26, which extends to the front waist area of the user.

The method according to the present disclosure, which uses discontinuous mechanical fastening patches spaced apart on a web, provides the unique configuration of mechanical fastening patches on the fastening tab disclosed herein, advantageously allows for a finger lift region on the user's end portion of the fastening tab, and also provides a cost advantage since continuous strips of mechanical fastener are not used.

Selected Embodiments of the Disclosure

In a first embodiment, the present disclosure provides a fastening tab comprising: a substrate comprising
 a main portion with a first distance (d1) between a top edge and an opposing bottom edge; and
 a user's end portion extending from the main portion, the user's end portion having a top edge, an opposing bottom edge, and a side edge connecting the top edge and the opposing bottom edge, wherein a second distance (d2) between the top edge and the opposing bottom edge of the user's end portion is smaller than the first distance (d1);
a primary mechanical fastening patch having a side edge coterminous with the side edge of the user's end portion of the substrate, wherein the primary mechanical fastening patch has a third distance (d3) between a top edge and an opposing bottom edge, and wherein the third distance (d3) is smaller than the second distance (d2); and
first and second auxiliary mechanical fastening patches on the main portion of the substrate, with the first auxiliary fastening patch coterminous with the top edge of the main portion of the substrate and the second auxiliary fastening patch coterminous with the opposing bottom edge of the main portion of the substrate, wherein each of the first and second auxiliary fastening patches has a height (d4a and d4b) between a top edge and a opposing bottom edge that is smaller than the third distance (d3).

In a second embodiment, the present disclosure provides a fastening tab according to the first embodiment, wherein a sum of the height of the first auxiliary fastening patch (d4a) and the height of the second auxiliary fastening patch (d4b) is equal to the third distance (d3).

In a third embodiment, the present disclosure provides a fastening tab according to the first or second embodiment, wherein the primary mechanical fastening patch extends into the main portion of the substrate.

In a fourth embodiment, the present disclosure provides a fastening tab according to the third embodiment, wherein the primary mechanical fastening patch and the first and second auxiliary mechanical fastening patches are aligned in the main portion of the substrate.

In a fifth embodiment, the present disclosure provides a fastening tab according to any one of the first to fourth embodiments, wherein the main portion has a zone that is extensible in at least one direction.

In a sixth embodiment, the present disclosure provides a fastening tab according to any one of the first to fifth embodiments, prepared or preparable by a method comprising:
 providing a substrate web extending in a machine direction;
 attaching multiple discrete patches of mechanical fastener to the substrate web so that the multiple patches of mechanical fastener are separated in the machine direction; and
 cutting through the substrate web and the multiple patches of mechanical fastener in the machine direction with a continuous, meandering cut to provide two sub-webs, each sub-web having first and second cut portions of the multiple patches of mechanical fastener.

In a seventh embodiment, the present disclosure provides a fastening tab according to the sixth embodiment, wherein the method further comprises providing cross-web direction cuts through each sub-web to provide a plurality of the fastening tabs, wherein providing cross-web direction cuts through each sub-web comprises cutting through the second cut portions of the multiple patches of mechanical fastener.

In an eighth embodiment, the present disclosure provides a fastening tab according to the sixth or seventh embodiment, wherein the continuous meandering cut has an undulating pattern.

In a ninth embodiment, the present disclosure provides a fastening tab according to any one of the sixth to eighth embodiments, wherein the multiple discrete patches of mechanical fastener are centered on the substrate web, and wherein the continuous meandering cut is centered on the substrate web.

In a tenth embodiment, the present disclosure provides a fastening tab according to any one of the sixth to eighth embodiments, wherein the multiple discrete patches of mechanical fastener are staggered in the cross web direction in a central portion of the substrate web.

In an eleventh embodiment, the present disclosure provides a web comprising multiple fastening tabs, each according to any one of the first through tenth embodiments, wherein the multiple fastening tabs are connected together at lines of weakness.

In a twelfth embodiment, the present disclosure provides an absorbent article having at least a front waist region, a rear waist region, and a longitudinal center line bisecting the front waist region and the rear waist region, wherein at least one of the front waist region or the rear waist region comprises a fastening tab according to any one of the first through tenth embodiments.

In a thirteenth embodiment, the present disclosure provides a web comprising:
 a substrate web extending in a machine direction and having a cross web direction and left and right longitudinal edges;
 multiple discrete patches of mechanical fastener, separated in the machine direction, and attached to the substrate web; and
 a meandering line of weakness extending in the machine direction through each of the multiple discrete patches of mechanical fastener to form first and second cut portions from each of the multiple discrete patches of mechanical fastener.

In a fourteenth embodiment, the present disclosure provides a web according to the thirteenth embodiment, further comprising multiple, staggered lines of weakness extending alternately from the left and right longitudinal edges to the meandering line of weakness, the multiple, staggered lines of weakness extending through the second cut portions of successive multiple discrete patches of mechanical fastener.

In a fifteenth embodiment, the present disclosure provides a web according to the thirteenth or fourteenth embodiment, wherein the multiple discrete patches of mechanical fastener are centered on the substrate web, and wherein the meandering line of weakness is centered on the substrate web.

In a sixteenth embodiment, the present disclosure provides a web according to the thirteenth or fourteenth embodiment, wherein the multiple discrete patches of mechanical fastener are staggered in the cross web direction in a central portion of the substrate web.

In a seventeenth embodiment, the present disclosure provides a web according to any one of the thirteenth to sixteenth embodiments, wherein the substrate web has at least two extensible zones that extend in the machine direction, the extensible zones being extensible at least in a direction at a non-zero angle to the machine direction.

In an eighteenth embodiment, the present disclosure provides a method of making fastening tabs, the method comprising:
 providing a substrate web extending in a machine direction;
 attaching multiple discrete patches of mechanical fastener to the substrate web so that the multiple patches of mechanical fastener are separated in the machine direction; and
 cutting through the substrate web and the multiple patches of mechanical fastener in the machine direction with a continuous, meandering cut to provide two sub-webs, each sub-web having first and second cut portions of the multiple patches of mechanical fastener.

In a nineteenth embodiment, the present disclosure provides a method of making fastening tabs according to the eighteenth embodiment, further comprising providing cross-web direction cuts through each sub-web to provide a plurality of fastening tabs, wherein the cross-web direction cuts cut through the second cut portions of the multiple patches of mechanical fastener.

In a twentieth embodiment, the present disclosure provides a method of making fastening tabs according to the eighteenth or nineteenth embodiment, wherein each of the plurality of fastening tabs comprises a first cut portion from one patch of mechanical fastener and a part of a second cut portion from each adjacent patch of mechanical fastener.

In a twenty-first embodiment, the present disclosure provides a method of making fastening tabs according to any one of the eighteenth to twentieth embodiments, wherein the substrate web has at least two extensible zones extending in the machine direction, the extensible zones being extensible in at least a direction at a non-zero angle to the machine direction.

In a twenty-second embodiment, the present disclosure provides a method of making fastening tabs according to any one of the eighteenth to twenty-first embodiments, wherein the continuous, meandering cut has an undulating pattern.

In a twenty-third embodiment, the present disclosure provides a method of making fastening tabs according to any one of the eighteenth to twenty-second embodiments, wherein the continuous, meandering cut is centered on the substrate web.

In a twenty-fourth embodiment, the present disclosure provides a method of making fastening tabs according to any one of the eighteenth to twenty-third embodiments, wherein the multiple discrete patches of mechanical fastener are provided in a single row, centered on the substrate web.

In a twenty-fifth embodiment, the present disclosure provides a method of making fastening tabs according to any one of the eighteenth to twenty-third embodiments, wherein the multiple discrete patches of mechanical fastener are staggered in the cross-web direction in a central portion of the substrate web.

In a twenty-sixth embodiment, the present disclosure provides a method of making fastening tabs according to any one of the eighteenth to twenty-fifth embodiments, wherein the multiple discrete patches of mechanical fastener are equivalent in size.

In a twenty-seventh embodiment, the present disclosure provides a method of making fastening tabs according to any one of the eighteenth to twenty-sixth embodiments, wherein the two sub-webs are separated before providing the cross-web direction cuts.

In a twenty-eighth embodiment, the present disclosure provides a method of making fastening tabs according to any one of the eighteenth to twenty-seventh embodiments, wherein the continuous, meandering cut defines the shape of a user's end portion of each fastening tab.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A fastening tab comprising:
 a substrate comprising:
  a main portion with a first distance (d1) between a top edge and an opposing bottom edge; and
  a user's end portion extending from the main portion, the user's end portion having a top edge, an opposing bottom edge, and a side edge connecting the top edge and the opposing bottom edge, wherein a second distance (d2) between the top edge and the opposing bottom edge of the user's end portion is smaller than the first distance (d1);
 a primary mechanical fastening patch having a side edge coterminous with the side edge of the user's end portion of the substrate, wherein the primary mechanical fastening patch has a third distance (d3) between a top edge and an opposing bottom edge, and wherein the third distance (d3) is smaller than the second distance (d2); and
 first and second auxiliary mechanical fastening patches on the main portion of the substrate, with the first auxiliary fastening patch coterminous with the top edge of the main portion of the substrate and the second auxiliary fastening patch coterminous with the opposing bottom edge of the main portion of the substrate, wherein each of the first and second auxiliary fastening patches has a height (d4a and d4b) between a top edge and a opposing bottom edge that is smaller than the third distance (d3), wherein the first and second auxiliary mechanical fastening patches are spaced apart from the primary mechanical fastening patch.

2. A fastening tab according to claim 1, wherein the primary mechanical fastening patch extends into the main portion of the substrate.

3. A fastening tab according to claim 2, wherein the primary mechanical fastening patch and the first and second auxiliary mechanical fastening patches are aligned in the main portion of the substrate.

4. A fastening tab according to claim 1, wherein the main portion has a zone that is extensible in at least one direction.

5. A fastening tab according to claim 1, preparable by a method comprising:
providing a substrate web extending in a machine direction;
attaching multiple discrete patches of mechanical fastener to the substrate web so that the multiple patches of mechanical fastener are separated in the machine direction;
cutting through the substrate web and the multiple patches of mechanical fastener in the machine direction with a continuous, meandering cut to provide two sub-webs, each sub-web having first and second cut portions of the multiple patches of mechanical fastener; and
providing cross-web direction cuts through each sub-web to provide a plurality of the fastening tabs, wherein providing cross-web direction cuts through each sub-web comprises cutting through the second cut portions of the multiple patches of mechanical fastener.

6. A fastening tab according to claim 5, wherein the multiple discrete patches of mechanical fastener are centered on the substrate web, and wherein the continuous, meandering cut has an undulating pattern and is centered on the substrate web.

7. A fastening tab according to claim 5, wherein the multiple discrete patches of mechanical fastener are staggered in the cross web direction in a central portion of the substrate web.

8. An absorbent article having at least a front waist region, a rear waist region, and a longitudinal center line bisecting the front waist region and the rear waist region, wherein at least one of the front waist region or the rear waist region comprises a fastening tab according to claim 1.

9. A web comprising a plurality fastening tabs according to claim 1, the web comprising:
a substrate web extending in a machine direction and having a cross-web direction and left and right longitudinal edges;
multiple discrete patches of mechanical fastener, separated in the machine direction, and attached to the substrate web;
a meandering line of weakness extending in the machine direction through each of the multiple discrete patches of mechanical fastener to form first and second cut portions from each of the multiple discrete patches of mechanical fastener, and
multiple, staggered lines of weakness extending alternately from the left and right longitudinal edges to the meandering line of weakness, the multiple, staggered lines of weakness extending through the second cut portions of successive multiple discrete patches of mechanical fastener,
wherein the meandering line of weakness defines a shape of the user's end portion of each of the fastening tabs, and wherein each of the fastening tabs comprises a first cut portion from one patch of mechanical fastener to provide the primary mechanical fastening patch and a part of a second cut portion from each adjacent patch of mechanical fastener to provide the first and second auxiliary mechanical fastening patches.

10. A web according to claim 9, wherein the multiple discrete patches of mechanical fastener are centered on the substrate web, and wherein the meandering line of weakness is centered on the substrate web.

11. A web according to claim 9, wherein the multiple discrete patches of mechanical fastener are staggered in the cross web direction in a central portion of the substrate web.

12. A web according to claim 9, wherein the substrate web has at least two extensible zones that extend in the machine direction, the extensible zones being extensible at least in a direction at a non-zero angle to the machine direction.

13. A method of making fastening tabs according to claim 1, the method comprising:
providing a substrate web extending in a machine direction;
attaching multiple discrete patches of mechanical fastener to the substrate web so that the multiple patches of mechanical fastener are separated in the machine direction;
cutting through the substrate web and the multiple patches of mechanical fastener in the machine direction with a continuous, meandering cut to provide two sub-webs, each sub-web having first and second cut portions of the multiple patches of mechanical fastener, and
providing cross-web direction cuts through each sub-web to provide a plurality of the fastening tabs, wherein the cross-web direction cuts cut through the second cut portions of the multiple patches of mechanical fastener,
wherein the continuous, meandering cut defines a shape of the user's end portion of each of the fastening tabs, and wherein each of the plurality of fastening tabs comprises a first cut portion from one patch of mechanical fastener to provide the primary mechanical fastening patch and a part of a second cut portion from each adjacent patch of mechanical fastener to provide the first and second auxiliary mechanical fastening patches.

14. A method according to claim 13, wherein the substrate web has at least two extensible zones extending in the machine direction, the extensible zones being extensible at least in a direction at a non-zero angle to the machine direction.

15. A method according to claim 13, wherein the continuous, meandering cut has an undulating pattern that is centered on the substrate web.

16. A method according to claim 13, wherein the multiple discrete patches of mechanical fastener are provided in a single row, centered on the substrate web.

17. A method according to claim 13, wherein the multiple discrete patches of mechanical fastener are staggered in the cross-web direction in a central portion of the substrate web.

18. A method according to claim 13, wherein the multiple discrete patches of mechanical fastener are equivalent in size.

19. A method according to claim 13, wherein the two sub-webs are separated before providing the cross-web direction cuts.

20. A fastening tab comprising:
a substrate comprising:
- a main portion with a first distance (d1) between a top edge and an opposing bottom edge; and
- a user's end portion extending from the main portion, the user's end portion having a top edge, an opposing bottom edge, and a side edge connecting the top edge and the opposing bottom edge, wherein a second distance (d2) between the top edge and the opposing bottom edge of the user's end portion is smaller than the first distance (d1);

a primary mechanical fastening patch having a side edge coterminous with the side edge of the user's end portion of the substrate, wherein the primary mechanical fastening patch has a third distance (d3) between a top edge and an opposing bottom edge, and wherein the third distance (d3) is smaller than the second distance (d2); and first and second auxiliary mechanical fastening patches on the main portion of the substrate, with the first auxiliary fastening patch coterminous with the top edge of the main portion of the substrate and the second auxiliary fastening patch coterminous with the opposing bottom edge of the main portion of the substrate, wherein each of the first and second auxiliary fastening patches has a height (d4*a* and d4*b*) between a top edge and a opposing bottom edge that is smaller than the third distance (d3), and wherein a sum of the height of the first auxiliary fastening patch (d4*a*) and the height of the second auxiliary fastening patch (d4*b*) is equal to the third distance (d3).

\* \* \* \* \*